United States Patent [19]
Allen et al.

[11] Patent Number: 6,165,792
[45] Date of Patent: Dec. 26, 2000

[54] AMINO ACID TRANSPORTERS

[75] Inventors: Stephen M. Allen, Wilmington, Del.; Catherine J. Thopre, Cambridge, United Kingdom

[73] Assignee: E. I. du Pont de Nemours and Company, Wilmington, Del.

[21] Appl. No.: 09/370,253

[22] Filed: Aug. 9, 1999

Related U.S. Application Data

[60] Provisional application No. 60/097,222, Aug. 20, 1998.

[51] Int. Cl.[7] ............................. C12N 15/82; C12N 15/74; C12N 15/29; C12N 15/63
[52] U.S. Cl. .................. 435/419; 536/23.6; 536/24.1; 435/468; 435/471; 435/252.3
[58] Field of Search ...................... 435/419, 468, 435/471, 252.3; 536/23.6, 24.1; 800/320, 320.1

[56] References Cited

PUBLICATIONS

Ohgawara, et al. Uptake of Liposome–Encopsolating Plasmid DNA By Plant Proto Plasts and Molecular Fate of Foreign DNA Protoplasma vol. 116, pp. 145–148.

Chen and Bush (1997) Plant Physiol. 115:1127–1134.
NCBI General Identifier No. 5510817.
NCBI General Identifier No. 4716084.
NCBI General Identifier No. 2310110.
NCBI General Identifier No. 4716501.
NCBI General Identifier No. 4716085.
Verma and Hong (1996) Plant Physiol. 110–1051–1053.
Rentsch, D. et al., (1996) Plant Cell 8:1437–1446.
NCBI General Identifier No. 2213629.
NCBI General Idenfitier No. 2576361.
NCBI General Identifier No. 1769901.
NCBI General Identifer No. 1769903.

*Primary Examiner*—DAvid T. Fox
*Assistant Examiner*—Medino A. Ibraheim

[57] ABSTRACT

This invention relates to an isolated nucleic acid fragment encoding a amino acid transporter. The invention also relates to the construction of a chimeric gene encoding all or a portion of the amino acid transporter, in sense or antisense orientation, wherein expression of the chimeric gene results in production of altered levels of the amino acid transporter in a transformed host cell.

6 Claims, No Drawings

SEQUENCE LISTING

<160> NUMBER OF SEQ ID NOS: 18

<210> SEQ ID NO 1
<211> LENGTH: 1882
<212> TYPE: DNA
<213> ORGANISM: Hordeum vulgare

<400> SEQUENCE: 1

| | | | | | | |
|---|---|---|---|---|---|---|
| gcacgagcca | ccttctcctt | tgtgtgactc | ctccggccat | tgctggacgc | gcgctcggtg | 60 |
| ccggaagcca | tggggacgca | cgcctcgccg | gacaacaaca | cgccgcccaa | ggatgagagg | 120 |
| actgcacggg | agaaggcgat | cgatgactgg | cttcctatca | cgtcttcaag | gaaagcaaag | 180 |
| tggtggtact | cggccttcca | caatgtcacc | gccatggttg | gcgctggggt | gctcagcctc | 240 |
| ccctacgcca | tgtctgaact | cggttggggt | cctggcatcg | cagtgatgac | cttgtcttgg | 300 |
| atcatcacgg | tgtacacgct | gtggcagatg | gtggagatgc | acgagatggt | gccaggcaag | 360 |
| cggtttgaca | ggtaccatga | gcttggacag | catgccttcg | gtgacaagct | cggcctttgg | 420 |
| atcgtggtgc | cacagcagct | cgtcgtcgag | gtcagcctga | acattgtcta | catggtcact | 480 |
| ggcggcaact | cgctcaagaa | gttccacgac | gtgatctgtg | atggcaagtg | caaggacatc | 540 |
| aagcttacct | acttcatcat | gatcttcgcc | tctgtccact | tcgtgctctc | ccagctacca | 600 |
| aacttcaact | ccatctccgg | catctccctc | gccgcagccg | tcatgtcact | cagctactcg | 660 |
| acaattgctt | gggcgcctc | cttgcacaag | gggaaggagg | agaacgtgga | ctacagcctg | 720 |
| cgggcgtcga | cgacagcagg | gcaggtgttt | ggtttcttgg | ggggcctcgg | cgatgtggca | 780 |
| ttctcctact | ccggccacaa | tgtggtgcta | gaaattcagg | ctaccatccc | atcgacgccc | 840 |
| ggcaacccgt | ccaagaagcc | aatgtggaag | ggcgtggtgg | tggcctacat | catcatcgcc | 900 |
| gcctgctact | tcccggttgc | atttatcggc | tactgggcat | ttggcaacag | cgtcgacgac | 960 |
| aacatcctca | tcaccctcaa | caagcccaag | tggctcatcg | ccatggccaa | catgatggtc | 1020 |

```
gtcgttcacc tcatcggtag ctaccagatt tatgcgatgc cggtgtttga catgatggag    1080
acgtttctgg tgaagaagtt ggagttcgca ccaggcatta cgctccgtct gatcacccga    1140
actatctatg ttgccttcac gatgtttatc ggcatgagct cccgttctt cggtggtctc     1200 atcgggttct tggtgggct cgccttcgca ccgacgacct atttccttcc ctgcatcatg     1260
tggctcatca tctgcaagcc caggatattc agcctctcat ggttcaccaa ctggatttgc    1320
atcgtccttg gtgtgcttct gatgatcgtg cgcccatcg gagggctcag gcagatcatc     1380
atttctgcca agacatacaa gttctactca tagatcacta gaattaccgt tcatcatcat    1440
cgcctcgtga ttggcaattc tactgccaga ttttattttt tttctgtcct gcaaagaaga    1500
aagaccatgg ataccacggc ttgtcgcaga tgtcggacgg tctgcttagt ttagaccaga    1560
agagggatgt gtgttggggg tagatcgtga aggggtccag cccgcttcca gcgccgggag    1620
ttttcatgca tgtactctta ctattttgca gagcactagc tatgaaaaat aggcgtacgg    1680
attcatatat accatgagaa atatcaaatt aagtgcaaga tccatacatt gcgattgttc    1740
ttgcatagat tattccgcaa tgtatgggtt cttttcttt caaaaaaaaa aaaaaaaaa     1800 aaaaaaaaaa aaaaaaaaaa aaaaaaaaaa aaaaaaaaaa aaaaaaaaaa aaaaaaaaaa    1860
aaaaaaaaaa aaaaaaaaaa aa                                             1882
```

<210> SEQ ID NO 2
<211> LENGTH: 447
<212> TYPE: PRT
<213> ORGANISM: Hordeum vulgare

<400> SEQUENCE: 2

```
Met Gly Thr His Ala Ser Pro Asp Asn Asn Thr Pro Lys Asp Glu
  1               5                  10                  15

Arg Thr Ala Arg Glu Lys Ala Ile Asp Asp Trp Leu Pro Ile Thr Ser
             20                  25                  30

Ser Arg Lys Ala Lys Trp Trp Tyr Ser Ala Phe His Asn Val Thr Ala
         35                  40                  45

Met Val Gly Ala Gly Val Leu Ser Leu Pro Tyr Ala Met Ser Glu Leu
     50                  55                  60

Gly Trp Gly Pro Gly Ile Ala Val Met Thr Leu Ser Trp Ile Ile Thr
 65                  70                  75                  80

Val Tyr Thr Leu Trp Gln Met Val Glu Met His Glu Met Val Pro Gly
                 85                  90                  95

Lys Arg Phe Asp Arg Tyr His Glu Leu Gly Gln His Ala Phe Gly Asp
                100                 105                 110

Lys Leu Gly Leu Trp Ile Val Val Pro Gln Gln Leu Val Val Glu Val
            115                 120                 125

Ser Leu Asn Ile Val Tyr Met Val Thr Gly Gly Asn Ser Leu Lys Lys
        130                 135                 140

Phe His Asp Val Ile Cys Asp Gly Lys Cys Lys Asp Ile Lys Leu Thr
145                 150                 155                 160

Tyr Phe Ile Met Ile Phe Ala Ser Val His Phe Val Leu Ser Gln Leu
                165                 170                 175

Pro Asn Phe Asn Ser Ile Ser Gly Ile Ser Leu Ala Ala Val Met
            180                 185                 190

Ser Leu Ser Tyr Ser Thr Ile Ala Trp Gly Ala Ser Leu His Lys Gly
        195                 200                 205

Lys Glu Glu Asn Val Asp Tyr Ser Leu Arg Ala Ser Thr Thr Ala Gly
```

```
        210                 215                 220
Gln Val Phe Gly Phe Leu Gly Leu Gly Asp Val Ala Phe Ser Tyr
225                 230                 235                 240

Ser Gly His Asn Val Val Leu Glu Ile Gln Ala Thr Ile Pro Ser Thr
                245                 250                 255

Pro Gly Asn Pro Ser Lys Lys Pro Met Trp Lys Gly Val Val Ala
            260                 265                 270

Tyr Ile Ile Ala Ala Cys Tyr Phe Pro Val Ala Phe Ile Gly Tyr
        275                 280                 285

Trp Ala Phe Gly Asn Ser Val Asp Asp Asn Ile Leu Ile Thr Leu Asn
290                 295                 300

Lys Pro Lys Trp Leu Ile Ala Met Ala Asn Met Met Val Val His
305                 310                 315                 320

Leu Ile Gly Ser Tyr Gln Ile Tyr Ala Met Pro Val Phe Asp Met Met
                325                 330                 335

Glu Thr Phe Leu Val Lys Lys Leu Glu Phe Ala Pro Gly Ile Thr Leu
                340                 345                 350

Arg Leu Ile Thr Arg Thr Ile Tyr Val Ala Phe Thr Met Phe Ile Gly
                355                 360                 365

Met Ser Phe Pro Phe Phe Gly Gly Leu Ile Gly Phe Phe Gly Gly Leu
370                 375                 380

Ala Phe Ala Pro Thr Thr Tyr Phe Leu Pro Cys Ile Met Trp Leu Ile
385                 390                 395                 400

Ile Cys Lys Pro Arg Ile Phe Ser Leu Ser Trp Phe Thr Asn Trp Ile
                405                 410                 415

Cys Ile Val Leu Gly Val Leu Leu Met Ile Val Ala Pro Ile Gly Gly
                420                 425                 430

Leu Arg Gln Ile Ile Ile Ser Ala Lys Thr Tyr Lys Phe Tyr Ser
        435                 440                 445

<210> SEQ ID NO 3
<211> LENGTH: 1016
<212> TYPE: DNA
<213> ORGANISM: Zea mays

<400> SEQUENCE: 3
cgccgccgtc atgtcgctca gctactccac catcgcgtgg ggcgcgtcgg tgcacaaggg     60
gaggatgtcg ggcgtcgact accacctgcg cgcgaccacc acgccgggga aggtgttcgg    120
cttcttcggc gcgctggggg acgtggcgtt cgcctacgcc ggccacaacg tggtgctgga    180
gatccaggcc accatcccgt ccaccccga caagccgtcc aagaagccca tgtggaaggg    240
cgtggtggtc gcctacgtcg tggtggcgct ctgctacttc cccgtcgcgc tcatcggcta    300
ctgggcgttc ggaaacacgg tcgaggacaa catcctcatc acgctcagca agcccaagtg    360
gctcatcgcg ctcgccaaca tgatggtcgt cgtccatgtc atcggcagct accagatcta    420
tgccatgccg gtgtttgaca tgatagagac cgtgctggtg aagaagctgc gcttccctcc    480
cggcctcacg ctgcgtctga tcgctcggac cctctatgtt gcgttcacga tgttcatagc    540
catcaccttc cccttcttcg gtgggctgct cggtttcttc ggcgggttcg ccttcgcgcc    600
gaccacctat ttccttccct gcgtcatgtg gctcgcaatc tacaagccca agaggttcag    660
cctctcctgg ttgaccaact ggatgtgcat cattcttggg gtgctcctga tgattctgtc    720
gcccatcgga gggctccggc aaataataat ggacgcgaaa acctaccagt tctactcgtg    780
agctaccacc agccatgact tgtaagcacg attggagaaa tctgtcaaag cctcaaccac    840
```

-continued

```
gagtttttgt ttttgttttt tgtcatgcca aacacataca tatacgtact gttttttttaa    900 tattcaaagg tgttcttcgt ggcttgcgtg tgtacagtat tatgtgtatg agggagacat    960
aagtttaatg atgctggctg tcaaagataa tggcggttca attaaaaaaa aaaaaa      1016
```

<210> SEQ ID NO 4
<211> LENGTH: 259
<212> TYPE: PRT
<213> ORGANISM: Zea mays

<400> SEQUENCE: 4

```
Ala Ala Val Met Ser Leu Ser Tyr Ser Thr Ile Ala Trp Gly Ala Ser
 1               5                  10                  15

Val His Lys Gly Arg Met Ser Gly Val Asp Tyr His Leu Arg Ala Thr
            20                  25                  30

Thr Thr Pro Gly Lys Val Phe Gly Phe Phe Gly Ala Leu Gly Asp Val
        35                  40                  45

Ala Phe Ala Tyr Ala Gly His Asn Val Val Leu Glu Ile Gln Ala Thr
    50                  55                  60

Ile Pro Ser Thr Pro Asp Lys Pro Ser Lys Lys Pro Met Trp Lys Gly
65                  70                  75                  80

Val Val Val Ala Tyr Val Val Ala Leu Cys Tyr Phe Pro Val Ala
                85                  90                  95

Leu Ile Gly Tyr Trp Ala Phe Gly Asn Thr Val Glu Asp Asn Ile Leu
            100                 105                 110

Ile Thr Leu Ser Lys Pro Lys Trp Leu Ile Ala Leu Ala Asn Met Met
        115                 120                 125

Val Val Val His Val Ile Gly Ser Tyr Gln Ile Tyr Ala Met Pro Val
    130                 135                 140

Phe Asp Met Ile Glu Thr Val Leu Val Lys Lys Leu Arg Phe Pro Pro
145                 150                 155                 160

Gly Leu Thr Leu Arg Leu Ile Ala Arg Thr Leu Tyr Val Ala Phe Thr
                165                 170                 175

Met Phe Ile Ala Ile Thr Phe Pro Phe Phe Gly Gly Leu Leu Gly Phe
            180                 185                 190

Phe Gly Gly Phe Ala Phe Ala Pro Thr Thr Tyr Phe Leu Pro Cys Val
        195                 200                 205

Met Trp Leu Ala Ile Tyr Lys Pro Lys Arg Phe Ser Leu Ser Trp Leu
    210                 215                 220

Thr Asn Trp Met Cys Ile Ile Leu Gly Val Leu Leu Met Ile Leu Ser
225                 230                 235                 240

Pro Ile Gly Gly Leu Arg Gln Ile Ile Met Asp Ala Lys Thr Tyr Gln
                245                 250                 255

Phe Tyr Ser
```

<210> SEQ ID NO 5
<211> LENGTH: 1865
<212> TYPE: DNA
<213> ORGANISM: Oryza sativa

<400> SEQUENCE: 5

```
gcacgagtgt atcaacccctt cttcttcttc ttcttcttct tcttcttcct ctgatcctcc    60
attgctgcaa agaagaaga ggtagacgaa ggaggaggag atcaggtgat catgggact    120 caggtggcag ataactaccc accggccaag gatggccgga gcgcgcagga gaaggcgatc    180
```

-continued

```
gacgactggc ttcccatcac gtcgtccagg aacgccaagt ggtggtactc cgccttccac    240
aatgtcaccg ccatggtcgg cgccggcgtc ctcagcctcc cctacgccat gtccgagctc    300
ggctggggac ctggcatcgc ggtgctgatc ctgtcatgga tcatcacgct ctacacgctg    360
tggcagatgg tggagatgca cgagatggtg cccgggaagc ggttcgacag gtaccacgag    420
ctcgggcagc acgcgttcgg cgagaagctg gcctctgga tcgtggtgcc gcagcagctc     480
gtcgtcgagg tcggcgtcaa catcgtgtac atggtcaccg gcggcaagtc gctgaagaag    540
ttccacgacg tgctctgcga gggccacggc tgcaagaaca tcaagctcac ctacttcatc    600
atgatcttcg cctccgtcca cttcgtcctc tcgcagctcc caaacttcaa ctccatctcc    660
ggcgtgtccc tcgccgccgc cgtcatgtcg ctcagctact ccaccatcgc gtggggcgcg    720
tcggtggaca aggggaaggt ggccgacgtc gactaccacc tgcgcgccac gacgtcgacg    780
gggaaggtgt tcggcttctt cagcgcgctg gcgacgtcg cgttcgcgta cgcggggcac     840
aacgtggtgc tggagatcca ggcgaccatc ccgtcgacgc cggagaagcc gtccaagaag    900
ccgatgtgga agggcgtcgt cgtcgcctac atcatcgtcg cgctctgcta cttccccgtg    960
gcgctcgtcg gatactgggc gttcggcaac cacgtcgacg acaacatcct catcacgctc   1020
tccaggccca aatggctcat cgcgctcgca aacatgatgg tcgtcatcca tgtcatcggg   1080
agctaccaga tctacgccat gccggtgttc gacatgatcg agaccgtgct cgtcaagaag   1140
ctcagattcc ctcccggcct cacgcttcgc ctcatcgcaa gaacactcta cgttgcgttc   1200
accatgttca tcgcgatcac cttcccgttc ttcggtggat tgcttgggtt cttcggtgga   1260
ttcgccttcg cgccaactac ttacttcctt ccctgcatca tgtggctagc aatctacaag   1320
ccaagaaggt tcagtctctc atggttcacc aactggatct gcatcattct tggagtgatg   1380
ctcatgatcc tgtcaccaat cggaggactc cggcagatca tcatagatgc caagacatac   1440
aagttctact cgtagattac atgttcatca tagtaatctc atgtggctgc aagttcaagt   1500
tctactcata ggcacacatg atgaaaccag ttactgcaaa agttttttt ttagccaaca    1560 aaggaagaag aaagttcaac accaagttca tacattgtca ctacgacgat gatcttttga   1620
gacgtgtcat gcatgcatca gtcgttaatt atgtgactta attaaaaaca aagaggttgt   1680
gtttgtgcat tgtcgctggg ttaatcatac tgtgttttta tatttcaatc tactattata   1740
ttgtaggctg acatggaaa ctgtgtgcag aaagatgaaa gggatggata attactggtt    1800
gattcttttg ctttccaaaa aaaaaaaaaa aaaaaaaaa aaaaaaaaa aaaaaaaaaa     1860 aaaaa                                                              1865
```

<210> SEQ ID NO 6
<211> LENGTH: 447
<212> TYPE: PRT
<213> ORGANISM: Oryza sativa

<400> SEQUENCE: 6

```
Met Gly Thr Gln Val Ala Asp Asn Tyr Pro Pro Ala Lys Asp Gly Arg
  1               5                  10                  15

Ser Ala Gln Glu Lys Ala Ile Asp Asp Trp Leu Pro Ile Thr Ser Ser
             20                  25                  30

Arg Asn Ala Lys Trp Trp Tyr Ser Ala Phe His Asn Val Thr Ala Met
         35                  40                  45

Val Gly Ala Gly Val Leu Ser Leu Pro Tyr Ala Met Ser Glu Leu Gly
     50                  55                  60

Trp Gly Pro Gly Ile Ala Val Leu Ile Leu Ser Trp Ile Ile Thr Leu
```

```
                65                  70                  75                  80
        Tyr Thr Leu Trp Gln Met Val Glu Met His Glu Met Val Pro Gly Lys
                            85                  90                  95

Arg Phe Asp Arg Tyr His Glu Leu Gly Gln His Ala Phe Gly Glu Lys
                        100                 105                 110

Leu Gly Leu Trp Ile Val Val Pro Gln Gln Leu Val Val Glu Val Gly
                        115                 120                 125

Val Asn Ile Val Tyr Met Val Thr Gly Gly Lys Ser Leu Lys Lys Phe
                    130                 135                 140

His Asp Val Leu Cys Glu Gly His Gly Cys Lys Asn Ile Lys Leu Thr
        145                 150                 155                 160

Tyr Phe Ile Met Ile Phe Ala Ser Val His Phe Val Leu Ser Gln Leu
                        165                 170                 175

Pro Asn Phe Asn Ser Ile Ser Gly Val Ser Leu Ala Ala Val Met
                    180                 185                 190

Ser Leu Ser Tyr Ser Thr Ile Ala Trp Gly Ala Ser Val Asp Lys Gly
                    195                 200                 205

Lys Val Ala Asp Val Asp Tyr His Leu Arg Ala Thr Thr Ser Thr Gly
        210                 215                 220

Lys Val Phe Gly Phe Phe Ser Ala Leu Gly Asp Val Ala Phe Ala Tyr
        225                 230                 235                 240

Ala Gly His Asn Val Val Leu Glu Ile Gln Ala Thr Ile Pro Ser Thr
                        245                 250                 255

Pro Glu Lys Pro Ser Lys Lys Pro Met Trp Lys Gly Val Val Val Ala
                    260                 265                 270

Tyr Ile Ile Val Ala Leu Cys Tyr Phe Pro Val Ala Leu Val Gly Tyr
                    275                 280                 285

Trp Ala Phe Gly Asn His Val Asp Asp Asn Ile Leu Ile Thr Leu Ser
            290                 295                 300

Arg Pro Lys Trp Leu Ile Ala Leu Ala Asn Met Met Val Val Ile His
        305                 310                 315                 320

Val Ile Gly Ser Tyr Gln Ile Tyr Ala Met Pro Val Phe Asp Met Ile
                        325                 330                 335

Glu Thr Val Leu Val Lys Lys Leu Arg Phe Pro Pro Gly Leu Thr Leu
                        340                 345                 350

Arg Leu Ile Ala Arg Thr Leu Tyr Val Ala Phe Thr Met Phe Ile Ala
                    355                 360                 365

Ile Thr Phe Pro Phe Phe Gly Leu Leu Gly Phe Phe Gly Gly Phe
            370                 375                 380

Ala Phe Ala Pro Thr Thr Tyr Phe Leu Pro Cys Ile Met Trp Leu Ala
        385                 390                 395                 400

Ile Tyr Lys Pro Arg Arg Phe Ser Leu Ser Trp Phe Thr Asn Trp Ile
                        405                 410                 415

Cys Ile Ile Leu Gly Val Met Leu Met Ile Leu Ser Pro Ile Gly Gly
                    420                 425                 430

Leu Arg Gln Ile Ile Ile Asp Ala Lys Thr Tyr Lys Phe Tyr Ser
                    435                 440                 445

<210> SEQ ID NO 7
<211> LENGTH: 430
<212> TYPE: DNA
<213> ORGANISM: Glycine max
<220> FEATURE:
<221> NAME/KEY: unsure
<222> LOCATION: (283)
```

```
<220> FEATURE:
<221> NAME/KEY: unsure
<222> LOCATION: (291)
<220> FEATURE:
<221> NAME/KEY: unsure
<222> LOCATION: (416)..(417)..(418)
<220> FEATURE:
<221> NAME/KEY: unsure
<222> LOCATION: (427)

<400> SEQUENCE: 7
atttcctctt tcattgaaga aaatttcata gcctcctctt aattacttaa tactgctaac      60
aaccatagac acaaaagtgc atatacttca caaccatggg aaccgagact ccgacgagtg     120
gaaatcctat tgcttcaggg ggagaaaagg ttgctttccc agcagcagag attgataaaa     180
gaacagcgga gcagaaggca attgatgatt ggcttcccat aacttcttca aggaacgcaa     240
aatggtggta ctcagctttt cacaacgtca ctgccatggt tgngagctgg ngttctaagc     300
cttccttctg ccatggcaag tcttgggatg gggcctgggg tggtgattct tgtattgtca     360
tgggataatc acactctaca cactatggca aatggtggag atgcatgaga tgggcnnngg     420 gaaaaangtt                                                            430

<210> SEQ ID NO 8
<211> LENGTH: 109
<212> TYPE: PRT
<213> ORGANISM: Glycine max
<220> FEATURE:
<221> NAME/KEY: UNSURE
<222> LOCATION: (63)
<220> FEATURE:
<221> NAME/KEY: UNSURE
<222> LOCATION: (90)
<220> FEATURE:
<221> NAME/KEY: UNSURE
<222> LOCATION: (107)

<400> SEQUENCE: 8

Met Gly Thr Glu Thr Pro Thr Ser Gly Asn Pro Ile Ala Ser Gly Gly
 1               5                  10                  15

Glu Lys Val Ala Phe Pro Ala Ala Glu Ile Asp Lys Arg Thr Ala Glu
            20                  25                  30

Gln Lys Ala Ile Asp Asp Trp Leu Pro Ile Thr Ser Ser Arg Asn Ala
        35                  40                  45

Lys Trp Trp Tyr Ser Ala Phe His Asn Val Thr Ala Met Val Xaa Ala
    50                  55                  60

Gly Val Leu Ser Leu Pro Ser Ala Met Ala Ser Leu Gly Met Gly Pro
65                  70                  75                  80

Gly Val Val Ile Leu Val Leu Ser Trp Xaa Ile Thr Leu Tyr Thr Leu
                85                  90                  95

Trp Gln Met Val Glu Met His Gly Met Gly Xaa Gly Lys
            100                 105

<210> SEQ ID NO 9
<211> LENGTH: 1703
<212> TYPE: DNA
<213> ORGANISM: Triticum aestivum

<400> SEQUENCE: 9
ctcacacatc ccctctgtt ctgtttactc tccattgctc aagacaaggc ccggccggca      60
gaacatgggg acgcaggcag cggagaactt cgaaccgccg ccaaggatg tcaggacgga     120 tgagcagaag aagattgacg actggctccc gatcacgtcg tcgaggaacg ccaagtggtg     180
```

-continued

```
gtactcggcc ttccacaatg tcaccgccat ggtcggcgcg ggggtgctca gcctccccta    240
cgccatgtcc gagctcggct ggggccctgg catcgcggtg ctggtcatct cgtgggtgat    300
cacgctctac acgctgtggc agatggtgga gatgcacgag atggtgcccg ggaagcggtt    360
cgacaggtac cacgagctcg ggcagcacgc cttcggcgac aagctggggc tgtggatcgt    420
ggtgccgcag cagctgatcg tggaggttgg cgtgaacatc gtgtacatgg tgaccggcgg    480
gaggtcgctc aagaagttcc acgacgtgat ctgcgacggc aagtgcaagg acatcaagct    540
caccttcttc atcatgatct cgcgtccgt gcacttcgtg ctctcgcagc tcccaaactt    600
gaactccatc tccggcgtgt ccctggccgc cgccgtcatg tcgctgtcct actcgaccat    660
cgcgtggggc gcgtcggtgg acaaggggaa gatggtggac gtggactaca acctccgcgc    720
caccacgacg ccggggaagg tgttcggctt cttcggggcg ctgggcgagg tggcgttcgc    780
gtacgccgga cacaacgtgg tgctggagat ccaggccacc atcccgtcca cgccggagaa    840
gccgtccaag aagcccatgt ggaagggcgt ggtggtggcc tacatcgtcg tcgcgctctg    900
ctacttcccc gtcgccctca tcggctactg ggccttcggc aacagcgtcg acgacaacat    960
cctcatcacc ctcaacaagc ccacctggct catctccacc gccaacatga tggttgtcat    1020
ccatgtcatc ggaagctacc agatttacgc gatgccggtg ttcgacatga tcgagacggt    1080
gctagtgaag aagctcaagt ccctcccgg cctcacgctc cgcttgattg cccggaccct    1140
ctatgttgcg ttcaccatgt tcgtcgccat caccttccct ttcttcggtg gcctgctcgg    1200
attcttcggc gggttcgcct ttgcgcccac gacatacttc ctgccctgca tcatgtggct    1260
cgccatctac aagcccaaaa gattcagcct ctcatggttc accaactggg tctgcatcgt    1320
ccttggagtg tgcctcatga tcctgtcgcc aatcggaggg ctcagacaga tcatcttgga    1380
ttccaagaca tacaaattct actcatagac cacttctacg acgcattgtg tcctgtgaaa    1440
actgcaagag atcatttacg atgcctacca cgaactctct tgcttgcaaa ggaaaaagaa    1500
aggaacatca tagtaccacg aactgttaca gatgggacgt tagatgcata tggtcagaga    1560
aaatttggtt tagtcaaagc aaatgggatg tgtttgtggt taatcatgtg tacgtaatat    1620
atatggtgtg tggatttgac tctgggtact gtagaatcga caatctcttt ttctgctcaa    1680
acttgcatgg aaaaaaaaaa aaa                                           1703
```

<210> SEQ ID NO 10
<211> LENGTH: 447
<212> TYPE: PRT
<213> ORGANISM: Triticum aestivum

<400> SEQUENCE: 10

```
Met Gly Thr Gln Ala Ala Glu Asn Phe Glu Pro Pro Ala Lys Asp Val
 1               5                  10                  15

Arg Thr Asp Glu Gln Lys Lys Ile Asp Asp Trp Leu Pro Ile Thr Ser
             20                  25                  30

Ser Arg Asn Ala Lys Trp Trp Tyr Ser Ala Phe His Asn Val Thr Ala
         35                  40                  45

Met Val Gly Ala Gly Val Leu Ser Leu Pro Tyr Ala Met Ser Glu Leu
     50                  55                  60

Gly Trp Gly Pro Gly Ile Ala Val Leu Val Ile Ser Trp Val Ile Thr
 65                  70                  75                  80

Leu Tyr Thr Leu Trp Gln Met Val Glu Met His Glu Met Val Pro Gly
                 85                  90                  95
```

-continued

```
Lys Arg Phe Asp Arg Tyr His Glu Leu Gly Gln His Ala Phe Gly Asp
                100                 105                 110

Lys Leu Gly Leu Trp Ile Val Val Pro Gln Gln Leu Ile Val Glu Val
            115                 120                 125

Gly Val Asn Ile Val Tyr Met Val Thr Gly Gly Arg Ser Leu Lys Lys
        130                 135                 140

Phe His Asp Val Ile Cys Asp Gly Lys Cys Lys Asp Ile Lys Leu Thr
145                 150                 155                 160

Phe Phe Ile Met Ile Phe Ala Ser Val His Phe Val Leu Ser Gln Leu
                165                 170                 175

Pro Asn Leu Asn Ser Ile Ser Gly Val Ser Leu Ala Ala Ala Val Met
            180                 185                 190

Ser Leu Ser Tyr Ser Thr Ile Ala Trp Gly Ala Ser Val Asp Lys Gly
        195                 200                 205

Lys Met Val Asp Val Asp Tyr Asn Leu Arg Ala Thr Thr Thr Pro Gly
    210                 215                 220

Lys Val Phe Gly Phe Phe Gly Ala Leu Gly Glu Val Ala Phe Ala Tyr
225                 230                 235                 240

Ala Gly His Asn Val Val Leu Glu Ile Gln Ala Thr Ile Pro Ser Thr
                245                 250                 255

Pro Glu Lys Pro Ser Lys Lys Pro Met Trp Lys Gly Val Val Val Ala
            260                 265                 270

Tyr Ile Val Val Ala Leu Cys Tyr Phe Pro Val Ala Leu Ile Gly Tyr
        275                 280                 285

Trp Ala Phe Gly Asn Ser Val Asp Asp Asn Ile Leu Ile Thr Leu Asn
    290                 295                 300

Lys Pro Thr Trp Leu Ile Ser Thr Ala Asn Met Met Val Val Ile His
305                 310                 315                 320

Val Ile Gly Ser Tyr Gln Ile Tyr Ala Met Pro Val Phe Asp Met Ile
                325                 330                 335

Glu Thr Val Leu Val Lys Lys Leu Lys Phe Pro Pro Gly Leu Thr Leu
            340                 345                 350

Arg Leu Ile Ala Arg Thr Leu Tyr Val Ala Phe Thr Met Phe Val Ala
        355                 360                 365

Ile Thr Phe Pro Phe Phe Gly Gly Leu Leu Gly Phe Phe Gly Gly Phe
    370                 375                 380

Ala Phe Ala Pro Thr Thr Tyr Phe Leu Pro Cys Ile Met Trp Leu Ala
385                 390                 395                 400

Ile Tyr Lys Pro Lys Arg Phe Ser Leu Ser Trp Phe Thr Asn Trp Val
                405                 410                 415

Cys Ile Val Leu Gly Val Cys Leu Met Ile Leu Ser Pro Ile Gly Gly
            420                 425                 430

Leu Arg Gln Ile Ile Leu Asp Ser Lys Thr Tyr Lys Phe Tyr Ser
        435                 440                 445

<210> SEQ ID NO 11
<211> LENGTH: 1616
<212> TYPE: DNA
<213> ORGANISM: Zea mays

<400> SEQUENCE: 11
gcacgagatc accgtgctgt gctgcggcgg cctcgtcctc ctcctcctcc tcctccctcc     60
tgcccttttt ataggccgcc tccgcttcgt cgtcttggca agacctgccc ccgcgcctgc    120
aatcctacga caacagggcg ccgctcctcc tgcccgtcaa gatcatggac gccgccgccg    180
```

-continued

```
acgacaagcc ggaaatctcc gacgatacgg cccaccagat tagcgttgat ccttggtatc    240
aagttggctt cgtcctcaca accggggtca acagcgcata cgttctagga tactctggat    300
caatcatggt ccctctaggc tggatcggcg gcacatgcgg cctcctccta gctgccgcca    360
tatccatgta cgctaatgct cttcttgcac ggcttcatga agtcggtggc aaacgccata    420
tcagatacag agaccttgct ggacacatat atggaccgaa atttacggg cttacatggg     480 ctctgcagta cattaacctt ttcatgatca cactggctt tatcatctta gctggacaag     540
ctctcaaggc cacgtatgga ctgttcagtg atgatggagt tctgaaactc ccttactgca    600
ttgcgatatc aggattcgtc tgtgctcttt tcgccattgg aatcccttat ttatctgccc    660
tcaggatttg gttggggttc tccacgcttt tcagcctcat gtatattgtg atagcagttg    720
tgctgtcgtc gagagatggg ataaccgcac ctgcaaggga ttacagcatc cccaaatcat    780
cgcagtcaac tcgagtcttc actacgatag gttccatagc agaccttgtg tttgcttaca    840
acaccggcat gctgccagaa attcaggcaa ccatcaggcc tcctgtggtg aagaacatgg    900
agaaagctct atggttccag ttcaccattg gctccttgcc tctctatgct gtagtttttg    960
tgggttactg ggcttatggg tcctcaacat caggctacct cctcaacagt gtcacaggcc   1020
cagtctgggt gaaagcggtt gcaaatctgt cggcattttt tcagacagtc atagcgctgc   1080
acatctttgc tagccccatg tatgaattcc tggacacaaa atatggaagt gggcgtggtg   1140
gcccttttga gatccacaac gtggcgttca gagtagcagt cagaggaggc tacctgacgg   1200
tgaacacgct ggtggccgcg gtgctcccat tcctcggcga cttcatgagc ctgacgggcg   1260
ccctcagcac cttcccgctg acgtttgtgc tcgcaaatca catgtacctg atggtgaagg   1320
ggcctaagct gggtgccatc cagaaatcat ggcactggct caatgttctt gggttcactg   1380
cgctggctgt tgcagcggcg gtctccgcaa taaggctcat catgcgtgat ccagcaccct   1440
accacttctt cgctgatctt tgagatcgat cgttttcttt tctttttgtt ggaatgctga   1500
gccagagcta gtattttttc attttcagag aattattatc catgtatgta aggatgacgc   1560 atatatat   tgaatagatg atttaatatc aaaaaaaaaa aaaaaaaaaa ccggca       1616
```

<210> SEQ ID NO 12
<211> LENGTH: 432
<212> TYPE: PRT
<213> ORGANISM: Zea mays

<400> SEQUENCE: 12

```
Met Asp Ala Ala Ala Asp Asp Lys Pro Glu Ile Ser Asp Asp Thr Ala
  1               5                  10                  15

His Gln Ile Ser Val Asp Pro Trp Tyr Gln Val Gly Phe Val Leu Thr
             20                  25                  30

Thr Gly Val Asn Ser Ala Tyr Val Leu Gly Tyr Ser Gly Ser Ile Met
         35                  40                  45

Val Pro Leu Gly Trp Ile Gly Gly Thr Cys Gly Leu Leu Ala Ala
     50                  55                  60

Ala Ile Ser Met Tyr Ala Asn Ala Leu Leu Ala Arg Leu His Glu Val
 65                  70                  75                  80

Gly Gly Lys Arg His Ile Arg Tyr Arg Asp Leu Ala Gly His Ile Tyr
                 85                  90                  95

Gly Pro Lys Ile Tyr Gly Leu Thr Trp Ala Leu Gln Tyr Ile Asn Leu
            100                 105                 110

Phe Met Ile Asn Thr Gly Phe Ile Ile Leu Ala Gly Gln Ala Leu Lys
```

```
                115                 120                 125
Ala Thr Tyr Gly Leu Phe Ser Asp Asp Gly Val Leu Lys Leu Pro Tyr
    130                 135                 140

Cys Ile Ala Ile Ser Gly Phe Val Cys Ala Leu Phe Ala Ile Gly Ile
145                 150                 155                 160

Pro Tyr Leu Ser Ala Leu Arg Ile Trp Leu Gly Phe Ser Thr Leu Phe
                165                 170                 175

Ser Leu Met Tyr Ile Val Ile Ala Val Val Leu Ser Ser Arg Asp Gly
            180                 185                 190

Ile Thr Ala Pro Ala Arg Asp Tyr Ser Ile Pro Lys Ser Ser Gln Ser
        195                 200                 205

Thr Arg Val Phe Thr Thr Ile Gly Ser Ile Ala Asp Leu Val Phe Ala
    210                 215                 220

Tyr Asn Thr Gly Met Leu Pro Glu Ile Gln Ala Thr Ile Arg Pro Pro
225                 230                 235                 240

Val Val Lys Asn Met Glu Lys Ala Leu Trp Phe Gln Phe Thr Ile Gly
                245                 250                 255

Ser Leu Pro Leu Tyr Ala Val Val Phe Val Gly Tyr Trp Ala Tyr Gly
            260                 265                 270

Ser Ser Thr Ser Gly Tyr Leu Leu Asn Ser Val Thr Gly Pro Val Trp
        275                 280                 285

Val Lys Ala Val Ala Asn Leu Ser Ala Phe Phe Gln Thr Val Ile Ala
    290                 295                 300

Leu His Ile Phe Ala Ser Pro Met Tyr Glu Phe Leu Asp Thr Lys Tyr
305                 310                 315                 320

Gly Ser Gly Arg Gly Gly Pro Phe Glu Ile His Asn Val Ala Phe Arg
                325                 330                 335

Val Ala Val Arg Gly Gly Tyr Leu Thr Val Asn Thr Leu Val Ala Ala
            340                 345                 350

Val Leu Pro Phe Leu Gly Asp Phe Met Ser Leu Thr Gly Ala Leu Ser
        355                 360                 365

Thr Phe Pro Leu Thr Phe Val Leu Ala Asn His Met Tyr Leu Met Val
    370                 375                 380

Lys Gly Pro Lys Leu Gly Ala Ile Gln Lys Ser Trp His Trp Leu Asn
385                 390                 395                 400

Val Leu Gly Phe Thr Ala Leu Ala Val Ala Ala Val Ser Ala Ile
                405                 410                 415

Arg Leu Ile Met Arg Asp Ser Ser Thr Tyr His Phe Phe Ala Asp Leu
            420                 425                 430

<210> SEQ ID NO 13
<211> LENGTH: 548
<212> TYPE: DNA
<213> ORGANISM: Oryza sativa

<400> SEQUENCE: 13
gcacgagctt acactccaga ttccctcctc catcgaatct ctgatatttg gagggagcga      60
ctcgacgcag catcgcatcg taaggaaggt cccctccact gtcgatggat cagcaccagc    120
tcgacgagga gaaccagaga gccgcgctct tccactcctc tgccccatct tcctcttttgg   180 gagctgacgg ggaaggagga gagggagact gtgccgctgc tgtcctgcaa gatggccgac    240
gataaatctg acactgtcca ggtctccgag gatacggcgc accagattag cattgatccc    300
tggtatcaag ttggattcat tctgacaacc ggggtgaata gtgcatatgt tctgggatat    360
```

```
tctgcatcaa tcatggtccc tttacgctgg tttggtggga catgtggctt gattctagct     420
gctgcaatat ccatgtttgc aaatgctcct cttgctcacc ttcatgaagt tgtgggaaa     480 cgccatatca gatacagaga tcttgctggg cacatatatg gtagaaaaat gtatcgctta     540
catgagcg                                                              548
```

```
<210> SEQ ID NO 14
<211> LENGTH: 103
<212> TYPE: PRT
<213> ORGANISM: Oryza sativa

<400> SEQUENCE: 14
```

Met Ala Asp Asp Lys Ser Asp Thr Val Gln Val Ser Glu Asp Thr Ala
 1               5                  10                  15

His Gln Ile Ser Ile Asp Pro Trp Tyr Gln Val Gly Phe Ile Leu Thr
            20                  25                  30

Thr Gly Val Asn Ser Ala Tyr Val Leu Gly Tyr Ser Ala Ser Ile Met
        35                  40                  45

Val Pro Leu Arg Trp Phe Gly Gly Thr Cys Gly Leu Ile Leu Ala Ala
    50                  55                  60

Ala Ile Ser Met Phe Ala Asn Ala Pro Leu Ala His Leu His Glu Val
65                  70                  75                  80

Cys Gly Lys Arg His Ile Arg Tyr Arg Asp Leu Ala Gly His Ile Tyr
                85                  90                  95

Gly Arg Lys Met Tyr Arg Leu
            100

```
<210> SEQ ID NO 15
<211> LENGTH: 447
<212> TYPE: DNA
<213> ORGANISM: Glycine max

<400> SEQUENCE: 15
```

```
gcacgaggca agtccaatgt atgagtattt ggataccaaa tatgggatca aagggagtgc      60
cctggctttc aagaacttgt catttcgagt cttggtaaga ggtggctacc tgactgtaaa     120
cacatttgta tcagctctgt tgccatttct tggagatttc atgagcctca ctggagctat     180
cagcacattt cccctcacat ttatccttgc aaaccatatg tacctagtga caaatgagaa     240
caaactaaca tccacccaaa agctctggca ttggatcaat atttgtttct ttgccctcat     300
gtctgctgcg gcagctattg cagccctgcg acttattgat ttagactcca aaacgtacca     360 tgttttgcg gatttatgat taaatgcatt atattctttc agtaattcta atgctagttt     420
gtgcttcaaa aaaaaaaaa aaaactc                                          447
```

```
<210> SEQ ID NO 16
<211> LENGTH: 125
<212> TYPE: PRT
<213> ORGANISM: Glycine max

<400> SEQUENCE: 16
```

His Glu Ala Ser Pro Met Tyr Glu Tyr Leu Asp Thr Lys Tyr Gly Ile
 1               5                  10                  15

Lys Gly Ser Ala Leu Ala Phe Lys Asn Leu Ser Phe Arg Val Leu Val
            20                  25                  30

Arg Gly Gly Tyr Leu Thr Val Asn Thr Phe Val Ser Ala Leu Leu Pro
        35                  40                  45

Phe Leu Gly Asp Phe Met Ser Leu Thr Gly Ala Ile Ser Thr Phe Pro

```
            50                  55                  60
Leu Thr Phe Ile Leu Ala Asn His Met Tyr Leu Val Thr Asn Glu Asn
 65                  70                  75                  80

Lys Leu Thr Ser Thr Gln Lys Leu Trp His Trp Ile Asn Ile Cys Phe
                 85                  90                  95

Phe Ala Leu Met Ser Ala Ala Ala Ile Ala Ala Leu Arg Leu Ile
            100                 105                 110

Asp Leu Asp Ser Lys Thr Tyr His Val Phe Ala Asp Leu
            115                 120                 125

<210> SEQ ID NO 17
<211> LENGTH: 570
<212> TYPE: DNA
<213> ORGANISM: Triticum aestivum
<220> FEATURE:
<221> NAME/KEY: unsure
<222> LOCATION: (425)
<220> FEATURE:
<221> NAME/KEY: unsure
<222> LOCATION: (459)
<220> FEATURE:
<221> NAME/KEY: unsure
<222> LOCATION: (466)
<220> FEATURE:
<221> NAME/KEY: unsure
<222> LOCATION: (480)
<220> FEATURE:
<221> NAME/KEY: unsure
<222> LOCATION: (493)
<220> FEATURE:
<221> NAME/KEY: unsure
<222> LOCATION: (514)
<220> FEATURE:
<221> NAME/KEY: unsure
<222> LOCATION: (533)
<220> FEATURE:
<221> NAME/KEY: unsure
<222> LOCATION: (556)
<220> FEATURE:
<221> NAME/KEY: unsure
<222> LOCATION: (568)

<400> SEQUENCE: 17
atttctcggc cctctaccag tactgctgct gctatacata tcacccaaac caaaccaaac      60
caaaccagac cgaacccatc catcgatcgc ctgccttcct tccagcgtat acatcgatag     120
agggtcgaag aagatggcca tgccgccggc ggagaaggtg atcgtggtgg acgccaaccc     180
ctccaagaac gggcacgggg acaagtttga tgacctgcct gtcgccgatg aaacctcaca     240
ccagattggc gttgatccat ggtaccaggt ggcgttcgtg ctgaccaccg gggtgaacag     300
cgcctacgtg ctgggctact cgggctcgct gatggtcccc gctgggctgg gttgggcggt     360
ccgtggggcc tcctcctggg ccgccgccgt gtccatgtac gccaactcgc tgctgggccg     420
cctcnactcc tggggcggca agcgtcacat caggtacang gactcnccgg cacatctacn     480
gggcccaaga ttncaagatc acctgggcat caantactca actcctcatg atnaacacag     540
gctcatcata atacanggca agcatcangg                                      570

<210> SEQ ID NO 18
<211> LENGTH: 118
<212> TYPE: PRT
<213> ORGANISM: Triticum aestivum
<220> FEATURE:
<221> NAME/KEY: UNSURE
<222> LOCATION: (69)
<220> FEATURE:
<221> NAME/KEY: UNSURE
```

-continued

```
<222> LOCATION: (79)..(80)..(81)
<220> FEATURE:
<221> NAME/KEY: UNSURE
<222> LOCATION: (97)
<220> FEATURE:
<221> NAME/KEY: UNSURE
<222> LOCATION: (108)
<220> FEATURE:
<221> NAME/KEY: UNSURE
<222> LOCATION: (115)

<400> SEQUENCE: 18

Met Ala Met Pro Pro Ala Glu Lys Val Ile Val Val Asp Ala Asn Pro
  1               5                  10                  15

Ser Lys Asn Gly His Gly Asp Lys Phe Asp Asp Leu Pro Val Ala Asp
             20                  25                  30

Glu Thr Ser His Gln Ile Gly Val Asp Pro Trp Tyr Gln Val Ala Phe
         35                  40                  45

Val Leu Thr Thr Gly Val Asn Ser Ala Tyr Val Leu Gly Tyr Ser Gly
     50                  55                  60

Ser Leu Met Val Xaa Leu Gly Trp Val Gly Arg Ser Val Gly Xaa Xaa
 65                  70                  75                  80

Xaa Ala Ala Ala Val Ser Met Tyr Ala Asn Ser Leu Leu Gly Arg Leu
                 85                  90                  95

Xaa Ser Trp Gly Gly Lys Arg His Ile Arg Tyr Xaa Asp Ser Pro Ala
            100                 105                 110

His Leu Xaa Gly Pro Arg
            115
```

AMINO ACID TRANSPORTERS

This application claims the benefit of U.S. Provisional Application Ser. No. 60/097,222, filed Aug. 20, 1998.

FIELD OF THE INVENTION

This invention is in the field of plant molecular biology. More specifically, this invention pertains to nucleic acid fragments encoding amino acid transporters in plants and seeds.

BACKGROUND OF THE INVENTION

Transport processes play an important role in nitrogen allocation in higher plants. Amino acids circulate through the vascular system with multiple possibilities for carrier-mediated interchange between phloem and xylem. There is a longstanding debate on the number and specificity of transport systems involved. To dissect the apparent complexity of amino acid transport at the physiological level, respective transporter genes have been isolated by complementation of yeast transport mutants.

An amino acid transporter from *Arabidopsis thaliana* was identified which is a high-affinity transporter for both lysine and histidine (Chen and Bush (1997) *Plant Physiol.* 115:1127–1134). This transporter (LHT1) is an integral membrane protein and has little affinity for arginine. LHT1 is present in all tissues, with strongest expression in young leaves, flowers, and siliques. A corn EST (NCBI General Identifier No. 5510817) and four rice ESTs (NCBI General Identifier Nos. 4716084, 2310110, 4716501 and 4716085) have sequence similarity with this *Arabidopsis thaliana* protein.

Under stress conditions, massive changes in partitioning of carbon and nitrogen take place. In transgenic tobacco overproduction of proline results in decreased tolerance to osmotic stress (Verma and Hong (1996) *Plant Physiol.* 110:1051–1053). Transforming a yeast mutant defective in amino acid transport with an *Arabidopsis thaliana* cDNA library, and selecting transformants on medium containing proline led to the identification of specific proline transporters (Rentsch, D. et al. (1996) *Plant Cell* 8:1437–1446). The two proline transporters (ProT1, and ProT2) are similar to each other and distantly related to amino acid permeases. ProT1 and ProT2 were found expressed in all organs analyzed, with higher levels of ProT1 mRNA being detected in root stems, and flowers. When plants are transferred to a solution containing 200 mM NaCl, ProT2 mRNA accumulated starting at 4 hours after initiation of treatment and increased with time.

SUMMARY OF THE INVENTION

The instant invention relates to isolated nucleic acid fragments encoding amino acid transporters. Specifically, this invention concerns an isolated nucleic acid fragment encoding a lysine- and histidine-specific transporter (LHT1) or a proline transporter and an isolated nucleic acid fragment that is substantially similar to an isolated nucleic acid fragment encoding an LHT1 or a proline transporter. In addition, this invention relates to a nucleic acid fragment that is complementary to the nucleic acid fragment encoding LHT1 or proline transporter.

An additional embodiment of the instant invention pertains to a polypeptide encoding all or a substantial portion of an amino acid transporter selected from the group consisting of LHT1 and proline transporter.

In another embodiment, the instant invention relates to a chimeric gene encoding an LHT1 or a proline transporter, or to a chimeric gene that comprises a nucleic acid fragment that is complementary to a nucleic acid fragment encoding an LHT1 or a proline transporter, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding an LHT1 or a proline transporter, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of an LHT1 or a proline transporter in a transformed host cell comprising: a) transforming a host cell with a chimeric gene comprising a nucleic acid fragment encoding an LHT1 or a proline transporter; and b) growing the transformed host cell under conditions that are suitable for expression of the chimeric gene wherein expression of the chimeric gene results in production of altered levels of LHT1 or proline transporter in the transformed host cell.

An addition embodiment of the instant invention concerns a method for obtaining a nucleic acid fragment encoding all or a substantial portion of an amino acid sequence encoding an LHT1 or a proline transporter.

BRIEF DESCRIPTION OF THE SEQUENCE LISTING

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Amino Acid Transporters

|  |  | SEQ ID NO: | |
|---|---|---|---|
| Protein | Clone Designation | (Nucleotide) | (Amino Acid) |
| Barley LHT1 | bsh1.pk0013.h9 | 1 | 2 |
| Corn LHT1 | cta1n.pk0048.h2 | 3 | 4 |
| Rice LHT1 | r1s48.pk0011.g8 | 5 | 6 |
| Soybean LHT1 | sfl1.pk0062.e1 | 7 | 8 |
| Wheat LHT1 | wlk4.pk0003.e2 | 9 | 10 |
| Corn Proline Transporter | cc71se-b.pk0008.a2 | 11 | 12 |
| Rice Proline | r10n.pk083.m21 | 13 | 14 |

TABLE 1-continued

Amino Acid Transporters

| | | SEQ ID NO: | |
|---|---|---|---|
| Protein | Clone Designation | (Nucleotide) | (Amino Acid) |
| Transporter | | | |
| Soybean Proline Transporter | sre.pk0035.d4 | 15 | 16 |
| Wheat Proline Transporter | w1m0.pk0010.e11 | 17 | 18 |

The Sequence Listing contains the one letter code for nucleotide sequence characters and the three letter codes for amino acids as defined in conformity with the IUPAC-IUBMB standards described in Nucleic Acids Research 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "nucleic acid fragment" is a polymer of RNA or DNA that is single- or double-stranded, optionally containing synthetic, non-natural or altered nucleotide bases. A nucleic acid fragment in the form of a polymer of DNA may be comprised of one or more segments of cDNA, genomic DNA or synthetic DNA.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-a-vis the ability to mediate gene silencing or alteration of the functional properties of the resulting protein molecule. It is therefore understood that the invention encompasses more than the specific exemplary nucleotide or amino acid sequences and includes functional equivalents thereof.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid fragments may also be characterized by their ability to hybridize. Estimates of such homology are provided by either DNA-DNA or DNA-RZNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6× SSC, 0.5% SDS at room temperature for 15 min, then repeated with 2× SSC, 0.5% SDS at 45° C. for 30 min, and then repeated twice with 0.2× SSC, 0.5% SDS at 50° C. for 30 min. A more preferred set of stringent conditions uses higher temperatures in which the washes are identical to those above except for the temperature of the final two 30 min washes in 0.2× SSC, 0.5% SDS was increased to 60° C. Another preferred set of highly stringent conditions uses two final washes in 0.1X SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Preferred are those nucleic acid fragments whose nucleotide sequences encode amino acid sequences that are 80% identical to the amino acid sequences reported herein. More preferred nucleic acid fragments encode amino acid sequences that are 90% identical to the amino acid sequences reported herein. Most preferred are nucleic acid fragments that encode amino acid sequences that are 95% identical to the amino acid sequences reported herein. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410; see also www.ncbi.nlm.nih.gov/BLASTO). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Molecular Biotechnology* 3:225).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature (London)* 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several amino acid transporters have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other LHT1s or proline transporters, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36: 1; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of lysine, histidine, or proline in those cells. Plants with altered levels of ProT2 may also show increased tolerance to salt and water stress.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective.

In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded amino acid transporter. An example of a vector for high level expression of the instant polypeptides in a bacterial host is provided (Example 7).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nature Genetics* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Beizer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various barley, corn, rice, soybean and wheat tissues were prepared. The characteristics of the libraries are described below.

TABLE 2 cDNA Libraries from Barley, Corn, Rice, Soybean and Wheat

| Library | Tissue | Clone |
|---|---|---|
| bsh1 | Barley Sheath, Developing Seedling | bsh1.pk0013.h9 |
| cc7lse-b | Corn Callus Type II Tissue, Somatic Embryo Formed | cc71se-b.pk0008.a2 |
| cta1n | Corn Tassel* | cta1n.pk0048.h2 |
| r10n | Rice 15 Day Old Leaf* | r10n.pk083.m21 |
| rls48 | Rice Leaf 15 Days After Germination, 48 Hours After Infection of Strain *Magaporthe grisea* 4360-R-67 (AVR2-YAMO); Susceptible | rls48.pk0011.g8 |
| sfl1 | Soybean Immature Flower | sfl1.pk0062.e1 |
| sre | Soybean Root Elongation Zone 4 to 5 Days After Germination | sre.pk0035.d4 |
| wlk4 | Wheat Seedlings 4 Hours After Treatment With Herbicide** | wlk4.pk0003.e2 |
| wlm0 | Wheat Seedlings 0 Hour After Inoculation With *Erysiphe graminis f. sp tritici* | wlm0.pk0010.e11 |

*These libraries were normalized essentially as described in U.S. Pat. No. 5,482,845, incorporated herein by reference.
**Application of 6-iodo-2-propoxy-3-propyl-4(3H)-quinazolinone; synthesis and methods of using this compound are described in USSN 08/545,827, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2

Identification of cDNA Clones cDNA clones encoding amino acid transporters were identified by conducting BLAST (Basic Local Alignment Search Tool; Altschul et al. (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding LHT1

The BLASTX search using the EST sequences from clones listed in Table 3 revealed similarity of the polypeptides encoded by the cDNAs to a putative amino acid transporter and LHT1 from *Arabidopsis thaliana* (NCBI General Identifier Nos. 2213629 and 2576361, respectively). Shown in Table 3 are the BLAST results for individual ESTs ("EST"), or the sequences of the entire cDNA inserts comprising the indicated cDNA clones ("FIS"):

TABLE 3

BLAST Results for Sequences Encoding Polypeptides Homologous to LHT1

| Clone | Status | BLAST pLog Score 2576361 | 2213629 |
|---|---|---|---|
| bsh1.pk0013.h9 | FIS | 254.00 | 254.00 |
| cta1n.pk0048.h2 | FIS | 102.00 | 111.00 |
| rls48.pk0011.g8 | EST | 254.00 | 254.00 |
| sfl1.pk0062.e1 | FIS | 23.50 | 23.40 |
| wlk4.pk0003.e2 | FIS | 254.00 | 254.00 |

BLAST analysis of the NCBI EST database indicates that: Nucleotides 272 through 780 from clone cta1n.pk0048.h2 are 99% identical to nucleotides 590 through 82 of a 590 nucleotide corn EST having NCBI General Identifier No. 5510817.

Nucleotides 976 through 1337 from clone rls48.pk0011.g8 are 99% identical to nucleotides 1 through 362 of a 362 nucleotide rice EST having NCBI General Identifier No. 4716084. Nucleotides 1 through 260 from clone rls48.pk0011.g8 are 98% identical to nucleotides 95 through 354 of a 370 nucleotide rice EST having NCBI General Identifier No. 2310110. Nucleotides 1122 through 1344 from clone rls48.pk0011.g8 are 100% identical to nucleotides 14 through 236 of a 340 nucloeotide rice EST having NCBI General Identifier No. 4716501. Nucleotides 1275 through 1344 from clone rls48.pk0011.g8 are 100% identical to nucleotides 1 through 70 of a 450 nucloeotide rice EST having NCBI General Identifier No. 4716085.

The data in Table 4 represents a calculation of the percent identity of the amino acid sequences set forth in SEQ ID NOs:2, 4, 6, 8 and 10 and the *Arabidopsis thaliana* (NCBI General Identifier Nos. 2213629 and 2576361) sequences.

TABLE 4

Percent Identity of Amino Acid Sequences Deduced From the Nucleotide Sequences of cDNA Clones Encoding Polypeptides Homologous to LHT1

| SEQ ID NO. | Percent Identity to 2213629 | 2576361 |
|---|---|---|
| 2 | 70.5 | 67.5 |
| 4 | 72.6 | 66.0 |
| 6 | 73.2 | 71.1 |
| 8 | 58.7 | 58.7 |
| 10 | 74.0 | 71.5 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode an entire or nearly entire barley, corn, rice and wheat LHT1 and a substantial portion of a soybean LHT1. These sequences represent a variant rice and the first barley, corn, soybean and wheat sequences encoding LHT1.

Example 3

Characterization of cDNA Clones Encoding Proline Transporter

The BLASTX search using the EST sequences from clones listed in Table 5 revealed similarity of the polypeptides encoded by the cDNAs to proline transporters from *Arabidopsis thaliana* (NCBI General Identifier Nos. 1769901 and 1769903). Shown in Table 5 are the BLAST results for individual ESTs ("EST"), or the sequences of the entire cDNA inserts comprising the indicated cDNA clones ("FIS"):

TABLE 5

BLAST Results for Sequences Encoding Polypeptides
Homologous to Proline Transporters

| | | BLAST pLog Score | |
|---|---|---|---|
| Clone | Status | 1769901 | 1769903 |
| cc71se-b.pk0008.a2 | FIS | 174.00 | |
| r10n.pk083.m21 | EST | 37.70 | 38.70 |
| sre.pk0035.d4 | EST | 48.52 | 48.70 |
| wlm0.pk0010.e11 | EST | 23.10 | 24.00 |

The data in Table 6 represents a calculation of the percent identity of the amino acid sequences set forth in SEQ ID NOs: 12, 14, 16 and 18 and the *Arabidopsis thaliana* (NCBI General Identifier Nos. 1769901 and 1769903) sequences.

TABLE 6

Percent Identity of Amino Acid Sequences Deduced
From the Nucleotide Sequences of cDNA Clones Encoding
Polypeptides Homologous to Proline Transporter

| | Percent Identity to | |
|---|---|---|
| SEQ ID NO. | 1769901 | 1769903 |
| 12 | 66.7 | 64.4 |
| 14 | 62.1 | 62.1 |
| 16 | 71.2 | 72.0 |
| 18 | 44.9 | 44.9 |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a corn, a rice, a soybean and a wheat proline transporters. These sequences represent the first corn, rice, soybean and wheat sequences encoding proline transporters.

Example 5

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML 103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML 103. Plasmid pML 103 has been deposited under the terms of the Budapest Treaty at ATCC (American Type Culture Collection, 10801 University Blvd., Manassas, Va. 20110–2209), and bears accession number ATCC 97366. The DNA segment from pML 103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 6

Expression of Chimeric Genes in Dicot Cells

A seed-specific expression cassette composed of the promoter and transcription terminator from the gene encoding the β subunit of the seed storage protein phaseolin from the bean Phaseolus vulgaris (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites NcoI (which includes the ATG translation initiation codon), SmaI, KpnI and XbaI. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature (London)* 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113–130). Cultures are grown in LB medium containing ampicillin (100 mg/L) at 25° C. At an optical density at 600 rn of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

What is claimed is:

1. An isolated nucleic acid fragment comprising a member selected from the group consisting of:
   (a) an isolated nucleic acid fragment encoding the amino acid sequence set forth in a member selected from the group consisting of SEQ ID NO: 2, SEQ ID NO: 4, SEQ ID NO: 6, SEQ ID NO: 8 and SEQ ID NO: 10; and
   (b) an isolated nucleic acid fragment that is complementary to (a).

2. The isolated nucleic acid fragment of claim 1 wherein nucleic acid fragment is a functional RNA.

3. The isolated nucleic acid fragment of claim 1 wherein the nucleotide sequence of the fragment comprises the sequence set forth in a member selected from the group consisting of SEQ ID NO:1, SEQ ID NO:3, SEQ ID NO:5, SEQ ID NO:7 and SEQ ID NO:9.

4. A chimeric gene comprising the nucleic acid fragment of claim 1 operably linked to at least one regulatory sequence not associated in nature with the nucleic acid fragment of claim 1.

5. A plant host cell transformed with the chimeric gene of claim 4.

6. A microbial host cell transformed with the chimeric gene of claim 4.

* * * * *